US00PP12115P2

(12) United States Plant Patent
van Dijk et al.

(10) Patent No.: US PP12,115 P2
(45) Date of Patent: Oct. 2, 2001

(54) ANTHURIUM PLANT NAMED 'PINK CHAMPION'

(75) Inventors: Jan van Dijk, Bleiswijk; N. A. M. van Rosmalen, Velp, both of (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 09/548,267

(22) Filed: Apr. 12, 2000

(51) Int. Cl.[7] ..... A01H 5/00
(52) U.S. Cl. ..... Plt./367
(58) Field of Search ..... Plt./367

*Primary Examiner*—Bruce R. Campell
*Assistant Examiner*—A Para
(74) *Attorney, Agent, or Firm*—Foley & Lardner

(57) ABSTRACT

A new and distinct cultivar of Anthurium plant named 'Pink Champion' characterized by having plants that flower early and fully and can be sold at different stages from a mini-type of 35 cm in height to a larger plant that is 70 cm in height. The peduncle of 'Pink Champion' is long and erect and therefore the flowers are held well above the foliage. The plant habit is full due to shoot formation, and the leaves are dark-green, compact and durable with light-green primary veins. The flowers are durable and, at first, are pink in color becoming green when maturing. The part of the spathe near the spadix turns first into green. After approximately 20 weeks, the flower becomes completely green. The green color of the spathe is lighter than the green color of the leaves. The amount of flowers is large in relation to the amount of leaf blades and therefore the ratio of leaf to flower size is excellent.

4 Drawing Sheets

BACKGROUND OF THE INVENTION

The present invention relates to a new and distinct cultivar of Anthurium plant, botanically known as *Anthurium andraeanum L.* and hereinafter referred to by the cultivar name 'Pink Champion'.

The new cultivar is a product of a planned breeding program, and was obtained from a cross made during such a program in Bleiswijk, The Netherlands, in 1993. The female or seed parent was a pink-red-colored, proprietary *Anthurium andraeanum* hybrid having selection number 93-372-02. The male or pollen parent was *Anthurium andraeanum* cultivar 'Sweet Heart Pink' (PBR No. 15142).

'Pink Champion' was discovered and selected as a flowering plant within the progeny of the stated cross by the inventors, Jan van Dijk and N. A. M. van Rosmalen in December 1995 in a controlled environment in a glasshouse in Bleiswijk, The Netherlands.

Asexual reproduction of the new cultivar by tissue culture was performed by the inventors in a controlled environment in Bleiswijk, The Netherlands, and has demonstrated that the combination of characteristics are herein disclosed for the new cultivar are firmly fixed and retained through successive generations of asexual reproduction.

BRIEF DESCRIPTION OF THE INVENTION

The following traits have been repeatedly observed and are determined to be basic characteristics of 'Pink Champion' which in combination distinguish this Anthurium as a new and distinct cultivar:

1. The plant flowers early and fully and can be sold at different stages from a mini-type of 35 cm in height to a larger plant that is 70 cm in height;
2. The peduncle is long and erect and therefore the flowers are held well-above the foliage;
3. The plant habit is full due to shoot formation;

4. The leaves are dark-green, compact and durable with light-green primary veins;
5. The flowers are durable and, at first, are pink in color becoming green when maturing. The part of the spathe near the spadix turns first into green. After approximately 20 weeks, the flower becomes completely green. The green color of the spathe is lighter than the green color of the leaves; and
6. The amount of flowers is large in relation to the amount of leaf blades and therefore the ratio of leaf to flower size is excellent.

'Pink Champion' has not been observed under all possible environmental conditions. The phenotype of the new cultivar may vary significantly with variations in environment such as temperature, light intensity, and daylength, without any change in genotype.

BRIEF DESCRIPTION OF THE DRAWINGS

The accompanying photographic illustrations show the characteristics of the foliage and flowers of a typical 'Pink Champion' plant, with colors being as true as possible with illustrations of this type.

Sheet 1 is a side view showing the flowers held well above the leaf canopy.

Sheet 2 is a close-up view of the flower showing the spathe and spadix.

Sheet 3 is a close-up view of the flowers of five different development stages. The flower on the left is the youngest while the one on the right with the green spadix and spathe is the oldest. As the flower matures, the spathe color turns from pink into green. The flowers on the left and right display a difference in age of approximately 25 weeks.

Sheet 4 is a close-up view of a leaf blade showing its green color with a shiny surface and light-green veins.

DETAILED BOTANICAL DESCRIPTION

The following observations, measurements and values describe 65 week old plants grown in Bleiswijk, The Netherlands, under greenhouse conditions which closely approximate those generally used in horticultural practice. Color references are made to The Royal Horticultural Society (R.H.S.) Colour Chart, except where general color terms of ordinary significance are used. The color references are approximate, as color depends to a degree on horticultural practices such as light level and degree of fertilization, among others. The color values were determined between 1:00 am. and 3:00 p.m. on Nov. 30, 1999 under 10,000 lux natural light in a glasshouse in Bleiswijk, The Netherlands.

Classification:

*Botanical.*—A hybrid of the species *Anthurium andraeanum L.*

*Commercial.*—Anthurium cv. 'Pink Champion'.

Parentage:

*Male parent.*—*Anthurium andraeanum* cultivar 'Sweet Heart Pink' PBR No. 15142).

*Female parent.*—*Anthurium andraeanum* hybrid having selection no. 93-372-02.

Propagation: Vegetative, by tissue culture.

Plant:

*Growth habit.*—Approximately 55–60 weeks following division, plant will reach a mature size of approximately 30 cm to 60 cm in height and approximately 35 cm to 55 cm in width in a 17-cm pot. When placed in a larger pot, plant may grow to approximately 80 cm in height.

Leaves:

*Form.*—The leaf blade is elliptical-cordate with an acute tip and a cordate base. The leaf blade angle with the petiole is between 110 and 140 degrees. Leaf blades enlarge as the plant ages and some axillary shoots with small leaf blades are also produced. Therefore, a wide range in leaf blade length and width is found on each plant. The miniumum leaf blade length is approximately 3 cm and the maximum leaf blade length is approximately 18 cm. The minimum leaf blade width is approximately 1.5 cm and the maximum leaf blade width is approximately 10 cm. Mature leaf blades are cupped.

*Margin.*—Weakly sinuate.

*Texture.*—Leaf blades are leathery and thick.

*Veins.*—The mid-vein and primary veins (the veins which radiate out from the juncture of the petiole and leaf) protrude at the underside of the leaf blade. The light-green color of the veins at the upper surface (RHS 144A) and the lower surface (RHS 144B) of the mid-vein and primary veins (approximately 6 to 8) contrast with the more darker-green color of the upper surface of the leaf blade.

*Color.*—The leaf blade upper surface is RHS 137A; the leaf blade lower surface is light-green (RHS 146B).

*Lobes.*—A leaf blade has two lobes extending past the petiole. The distance from petiole/leaf juncture to the highest point on the lobes of mature leaf blades (width 10 cm, length 15 cm) ranges approximately from 4 to 5 cm.

*Petiole.*—Green (RHS 146B); the cross section of the petiole is round and the diameter is approximately 2 to 5 mm, length is 10–15 cm. The color of the cataphylls surrounding the petioles is RHS 175A.

Spathe:

*Buds.*—The spathe is tightly rolled around the spadix and extrudes from the peduncle sheath. The spathe is fully open at approximately the same time that the peduncle fully elongates.

*Size.*—The completely developed spathe of a 40-cm tall plant is approximately 7 cm to 8 cm long and approximately 5 cm to 8 cm wide.

*Color.*—When just fully open, the upper surface is RHS 52B and the lower surface is RHS 51B. After approximately 10 weeks, the spathe is fully open and the lower surface starts to become green from the edge of the lobes (RHS 144A). The pink color slightly disappears. The rest of the spathe turns into a white/green/brown color. The primary veins in the spathe of a mature flower can fade to dark pink. After another 10 weeks, the spathe is completely green (RHS 144A). A little edge at the place where the spadix protrudes from the spathe stays pink.

*Arrangement.*—The spathe angle with the peduncle is between 100 and 120 degrees. The spathe stand on a straight wiry peduncle approximately 6 cm to 15 cm above the foliage. The peduncle cross-section is round and the diameter approximately 3 mm to 6 mm, depending on the age of the plant. The peduncle is erect and ranges from approximately 15 to 45 cm depending on the age of the plant.

*Shape.*—The spathe is cordate (heart-shaped) with a mucronate tip and a cordate base. A just fully opened spathe is cup-shaped. The lobes of the spathe stay upwards. As the flower ages, the tip bends upwards slightly.

*Flowering time.*—One small untreated tissue culture plant of approximately 2 cm in height will flower, depending on season, after approximately 16 to 17 months when approximately 3 to 4 blossoms will appear. More blossoms appear a few weeks later so that a full flowering and salable plant can have 6 to 9 pink flowers. Due to the long life of the flowers, green flowers are also visible on the plant. Smaller blossoms may occur on less mature growth.

Reproductive organs:

*Size.*—The spadix measures approximately 2.5 to 5.5 cm in height. The length of the spadix is smaller than the length of the spathe. The spadix is columnar in shape. The width of a mature spadix that is approximtely 5.5 cm long is approximately 11 mm to 12 mm at the base and approximately 8 mm to 9 mm at the top. The spadix angle with the spathe is approximately 75 to 85 degrees.

*Color.*—At the time the spathe unrolls, the spadix is divided into unripe and ripe portions. The unripe portion at the top side is yellow (RHS 20B) and the ripe portion at the base side is pink (RHS 48B). As the spadix matures, it becomes first fully pink and then turns slightly light-green. When the pistil has been pollinated, there will exist berries on the spadix. The spadix is then dark-green (RHS 137C).

*Stamens.*—Anthers and filaments are not clearly visible on the spadix.

*Pollen.*—White in color (RHS 155D).

*Pistil.*—The same color as described for the spadix. The pistil protrudes from the spadix.

Berries and seeds: Berries are oval and yellow-brown (RHS 169B to 169C); seeds are oval and oblate, yellow-green (RHS 151A).

Roots: Flesh cream-white (RHS 158A to 158B), roots with smaller hairy laterals. The root-tips are yellow.

I claim:

1. A new and distinct Anthurium plant named 'Pink Champion', as herein described and illustrated.

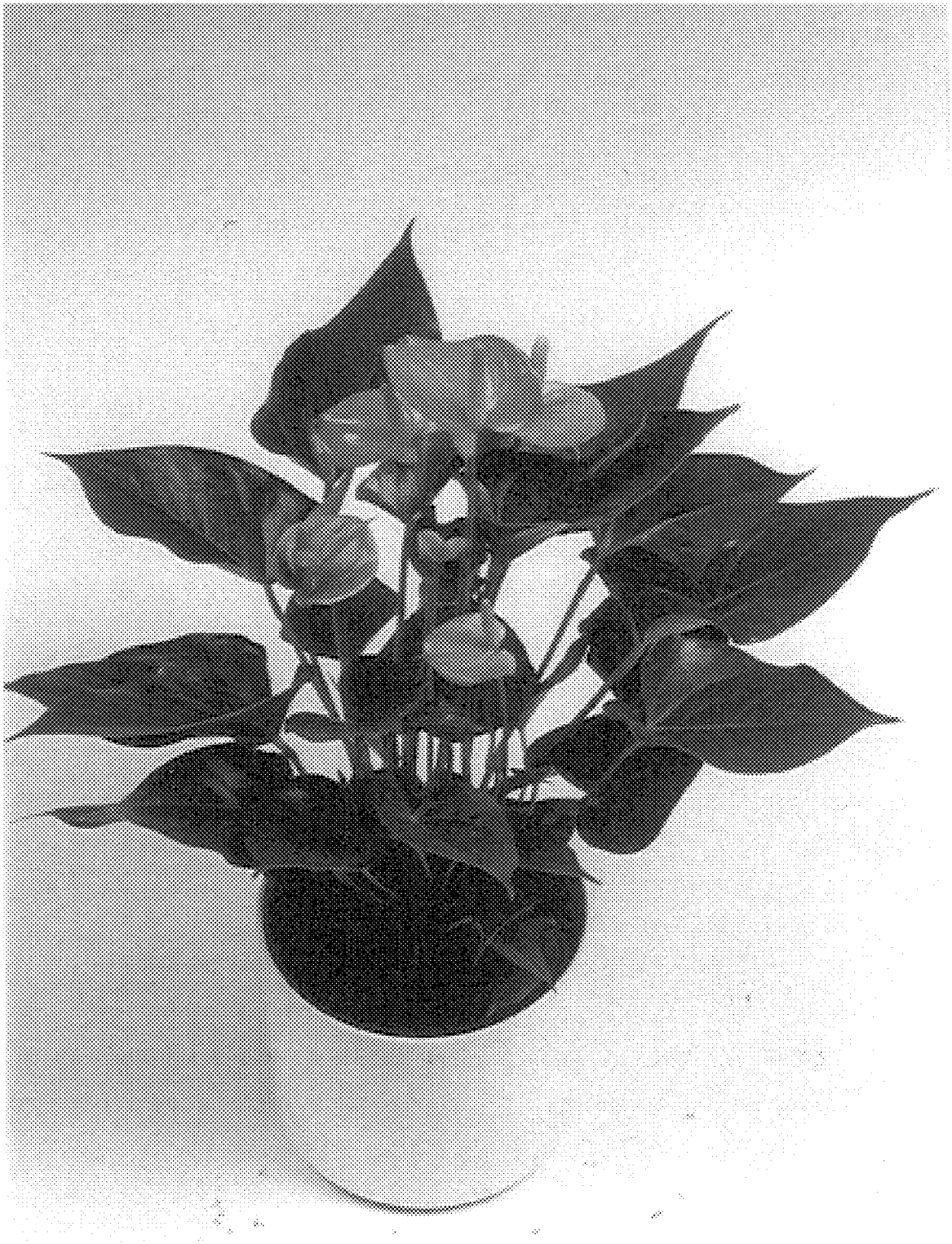

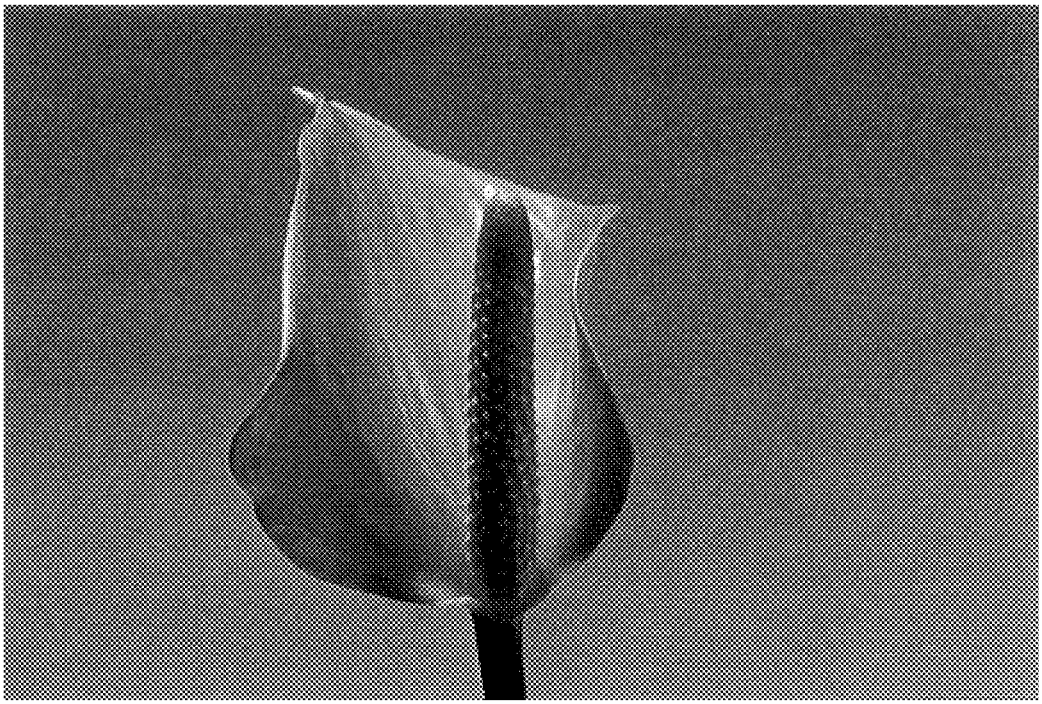

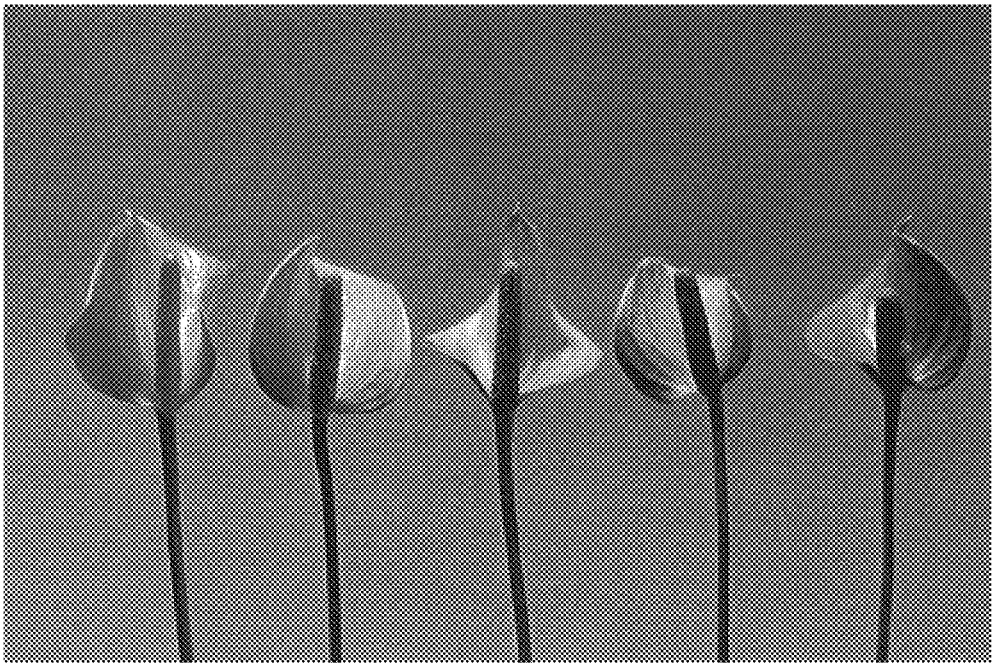

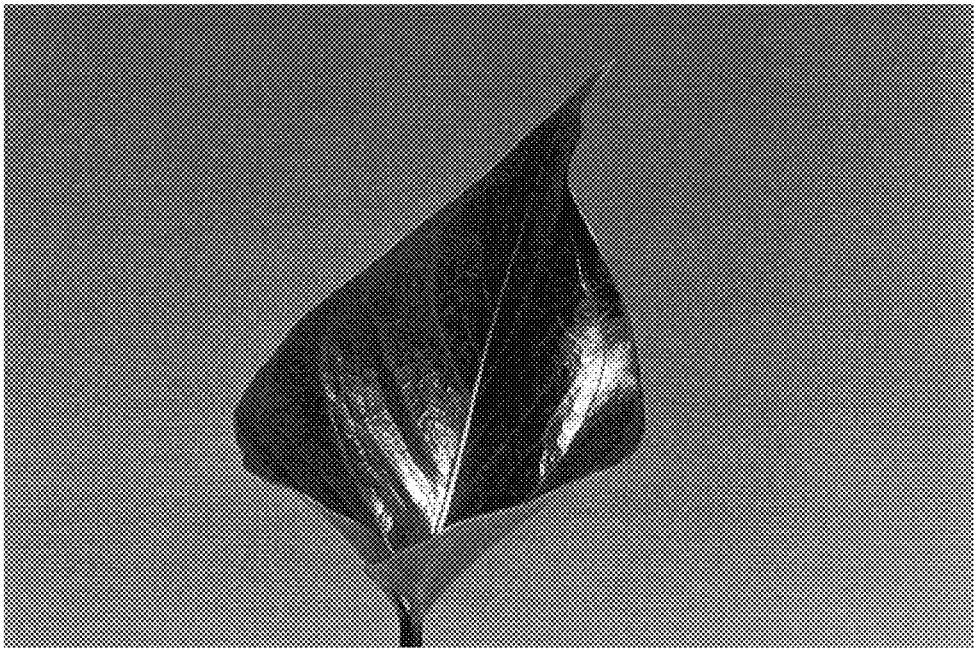

* * * * *